United States Patent
Lee et al.

(10) Patent No.: US 7,940,995 B2
(45) Date of Patent: May 10, 2011

(54) ULTRASOUND DIAGNOSTIC SYSTEM FOR AUTOMATICALLY DETECTING A BOUNDARY OF A TARGET OBJECT AND METHOD OF USING THE SAME

(75) Inventors: Ki Jong Lee, Yongin-si (KR); Hye Jung Kim, Gimpo-si (KR)

(73) Assignee: Medison Co., Ltd., Hongchun-gun (KR)

( * ) Notice: Subject to any disclaimer, the term of this patent is extended or adjusted under 35 U.S.C. 154(b) by 1562 days.

(21) Appl. No.: 11/274,330

(22) Filed: Nov. 16, 2005

(65) Prior Publication Data

US 2006/0173317 A1    Aug. 3, 2006

(30) Foreign Application Priority Data

Jan. 12, 2005    (KR) .................. 10-2005-0002958

(51) Int. Cl.
*G06K 9/40*    (2006.01)
(52) U.S. Cl. .................. 382/266; 382/103; 382/260
(58) Field of Classification Search .................. 382/254, 382/266, 275, 100, 103, 128, 134
See application file for complete search history.

(56) References Cited

U.S. PATENT DOCUMENTS

| | | | |
|---|---|---|---|
| 6,356,300 B1 * | 3/2002 | Shiba | 348/130 |
| 6,404,936 B1 * | 6/2002 | Katayama et al. | 382/283 |
| 7,072,499 B2 | 7/2006 | Deschamps et al. | |
| 7,466,848 B2 * | 12/2008 | Metaxas et al. | 382/128 |
| 2001/0031920 A1 * | 10/2001 | Kaufman et al. | 600/431 |
| 2002/0150280 A1 * | 10/2002 | Li | 382/117 |

FOREIGN PATENT DOCUMENTS

| | | |
|---|---|---|
| JP | 08-206117 | 8/1996 |
| JP | 10-191020 | 7/1998 |
| JP | 10-277033 | 10/1998 |
| JP | 11-201908 | 7/1999 |
| JP | 2003-199744 | 7/2003 |
| JP | 2004-510515 | 4/2004 |
| JP | 2005-58535 | 3/2005 |

OTHER PUBLICATIONS

Office Action issued in Japanese Patent Application No. 2005-333082 on Nov. 16, 2010.

* cited by examiner

*Primary Examiner* — Brian Q Le
*Assistant Examiner* — Edward Park
(74) *Attorney, Agent, or Firm* — Oblon, Spivak, McClelland, Maier & Neustadt, L.L.P.

(57) ABSTRACT

A method and a system of automatically detecting a boundary of a target object by using an ultrasound diagnostic image. In accordance with the present invention, the boundary of the target object can be detected automatically and precisely. The ultrasound diagnostic method and system form an edge detection boundary candidate model by detecting an edge of the ultrasound diagnostic image, forming a simplification boundary candidate model by performing a simplification operation to the edge detection boundary candidate model, forming a sessionization boundary candidate model by performing a sessionization operation to the simplification boundary candidate model, and detecting the boundary of the target object of the ultrasound diagnostic image based on the edge detection boundary candidate model, the simplification boundary candidate model and the sessionization boundary candidate model. In accordance with the present invention, the boundary of the target object is automatically detected by using the ultrasound diagnostic image to reduce any inconvenience to the user and solve the problem in which the measured result may vary with each user, which was caused by a conventional method of manually detecting the boundary.

20 Claims, 14 Drawing Sheets

|    | C0 | C1 | C2 | C3 | C4 |
|----|----|----|----|----|----|
| R0 | 1  | 1  | 0  | -1 | -1 |
| R1 | 1  | 1  | 0  | -1 | -1 |
| R2 | 1  | 1  | 0  | -1 | -1 |
| R3 | 1  | 1  | 0  | -1 | -1 |
| R4 | 1  | 1  | 0  | -1 | -1 |

Fig. 2A

|    | C0 | C1 | C2 | C3 | C4 |
|----|----|----|----|----|----|
| R0 | 1  | 1  | 1  | 1  | 1  |
| R1 | 1  | 1  | 1  | 1  | 1  |
| R2 | 0  | 0  | 0  | 0  | 0  |
| R3 | -1 | -1 | -1 | -1 | -1 |
| R4 | -1 | -1 | -1 | -1 | -1 |

Fig. 2B

|     | x0 | x1 | x2 | x3 | x4 | x5 | x6 | x7 |
|-----|----|----|----|----|----|----|----|----|
| y0  | 0  | 1  | 3  | 4  | 9  | 2  | 2  | 1  |
| y1  | 2  | 4  | 9  | 3  | 4  | 2  | 3  | 0  |
| y2  | 0  | 3  | 5  | 8  | 7  | 4  | 7  | 3  |
| y3  | 3  | 1  | 7  | 2  | 8  | 7  | 6  | 2  |
| y4  | 1  | 2  | 2  | 9  | 6  | 3  | 7  | 1  |
| y5  | 2  | 5  | 7  | 4  | 7  | 4  | 3  | 1  |
| y6  | 1  | 3  | 0  | 8  | 9  | 8  | 2  | 1  |
| y7  | 0  | 0  | 0  | 9  | 9  | 2  | 5  | 0  |

|     | x0 | x1 | x2 | x3 | x4 | x5 | x6 | x7 |
|-----|----|----|----|----|----|----|----|----|
| y0  | 0  | 1  | 3  | 4  | 9  | 2  | 2  | 1  |
| y1  | 2  | 4  | 9  | 3  | 4  | 2  | 3  | 0  |
| y2  | 0  | 3  | 5  | 8  | 7  | 4  | 7  | 3  |
| y3  | 3  | 1  | 7  | 2  | 8  | 7  | 6  | 2  |
| y4  | 1  | 2  | 2  | 9  | 6  | 3  | 7  | 1  |
| y5  | 2  | 5  | 7  | 4  | 7  | 4  | 3  | 1  |
| y6  | 1  | 3  | 0  | 8  | 9  | 8  | 2  | 1  |
| y7  | 0  | 0  | 0  | 9  | 9  | 2  | 5  | 0  |

ULTRASOUND DIAGNOSTIC SYSTEM FOR AUTOMATICALLY DETECTING A BOUNDARY OF A TARGET OBJECT AND METHOD OF USING THE SAME

FIELD OF THE INVENTION

The present invention generally relates to diagnostic systems, and more particularly to an ultrasound diagnostic system and method for automatically detecting a boundary of a target object by using an ultrasound diagnostic image.

BACKGROUND OF THE INVENTION

Nowadays, a diagnostic ultrasound system is widely used to inspect an internal state of a human body. The diagnostic ultrasound system may obtain an image of a single layer or a blood flow of a soft tissue without using an invasive needle. This is typically done through the process of radiating an ultrasound signal to a desired portion in the human body from a body surface of a target object to be diagnosed, receiving the reflected ultrasound signal, and processing the received ultrasound signal (the ultrasound echo signal.) Compared to other medical imaging systems (e.g., X-ray diagnostic system, X-ray Computerized Tomography (CT) scanner, Magnetic Resonance Imaging (MR) system, nuclear medicine diagnostic system, etc.), the ultrasound diagnostic system is relatively small in size and inexpensive, capable of displaying images in real-time, highly safe from exposure to X-ray radiation etc. Due to such advantages, the ultrasound diagnostic system is extensively employed to diagnose the heart, abdomen and urinary organs, especially in the fields of obstetrics and gynecology, etc.

In order to obtain precise information on a body structure and an organ to be inspected, it is necessary to quantitize an image obtained from the ultrasound diagnostic system. Conventionally, the body structure is passively quantitized based on a static image or measured information from the static image. For example, in order to measure a growth condition of an unborn child during pregnancy or on the expected date of delivery, the static image of the unborn child should be obtained during a lower activity period of the unborn child in his/her mother's body. Further, a contour or length of the unborn child should be measured from the obtained static image over a few times.

It is, however, difficult to obtain a static image of a continuously pumping organ such as the heart since the pumping of the heart leads to a constriction and an expansion of the organ and also causes a contour of the heart to vary continuously. In this regard, in order to completely evaluate a feature of the heart's function, a number of static images (e.g., more than 30 to 150 images) should be obtained during one cycle of heart pumping to detect a boundary of the heart by measuring necessary numerical values from the static images. In this case, the numerical values should be measured by setting a seed point or by designating a sample point of the boundary, thereby not only causing inconvenience in which an operator must be involved in the measurement, but also raising a problem in that the measured result may vary with each operator.

SUMMARY OF THE INVENTION

It is, therefore, an object of the present invention to provide an ultrasound diagnostic system and a method that can automatically detect a boundary of a target object by using the ultrasound diagnostic image.

In accordance with one aspect of the present invention, in order to achieve the above-mentioned objects, there is provided a method for detecting a boundary of a target object by using an ultrasound diagnostic image, including the steps of: (a) detecting an edge of the ultrasound diagnostic image to form an edge detection boundary candidate model; (b) performing a simplification operation upon the edge detection boundary candidate model to form a simplification boundary candidate model; (c) performing a sessionization operation upon the simplification boundary candidate model to form a sessionization boundary candidate model; and (d) detecting a boundary of the target object of the ultrasound diagnostic image based on the edge detection boundary candidate model, the simplification boundary candidate model and the sessionization boundary candidate model.

In accordance with another aspect of the present invention, there is provided an ultrasound diagnostic system, which transmits an ultrasound wave to a target object, receives an ultrasound signal reflected from the target object, thereby providing an ultrasound diagnostic image. The system includes an image processor, wherein the image processor includes: means for detecting an edge from the ultrasound diagnostic image to produce an edge detection boundary candidate model; means for performing a simplification operation upon the edge detection candidate model to produce a simplification boundary candidate model; means for performing a sessionization operation upon the simplification boundary candidate model to produce the sessionization boundary candidate model; and means for detecting a boundary of the target object of the ultrasound diagnostic image based on the edge detection boundary candidate model, the simplification boundary candidate model and the sessionization boundary candidate model.

BRIEF DESCRIPTION OF THE DRAWINGS

The above and other objects and features in accordance with the present invention will become apparent from the following descriptions of preferred embodiments given in conjunction with the accompanying drawings, in which:

FIG. 2A shows an exemplary filter for detecting a vertical edge of an ultrasound diagnostic image of the heart in accordance with one embodiment of the present invention.

FIG. 2B shows an exemplary filter for detecting a horizontal edge of an ultrasound diagnostic image of the heart in accordance with one embodiment of the present invention.

FIG. 4A is an exemplary diagram depicting an example of detecting a characteristic value of the filter by using a vertical edge detection filter in accordance with one embodiment of the present invention.

FIG. 4B is an exemplary diagram depicting an example of detecting a characteristic value of the filter by using a horizontal edge detection filter in accordance with one embodiment of the present invention.

DETAILED DESCRIPTION OF THE PRESENT INVENTION

Figure 1:
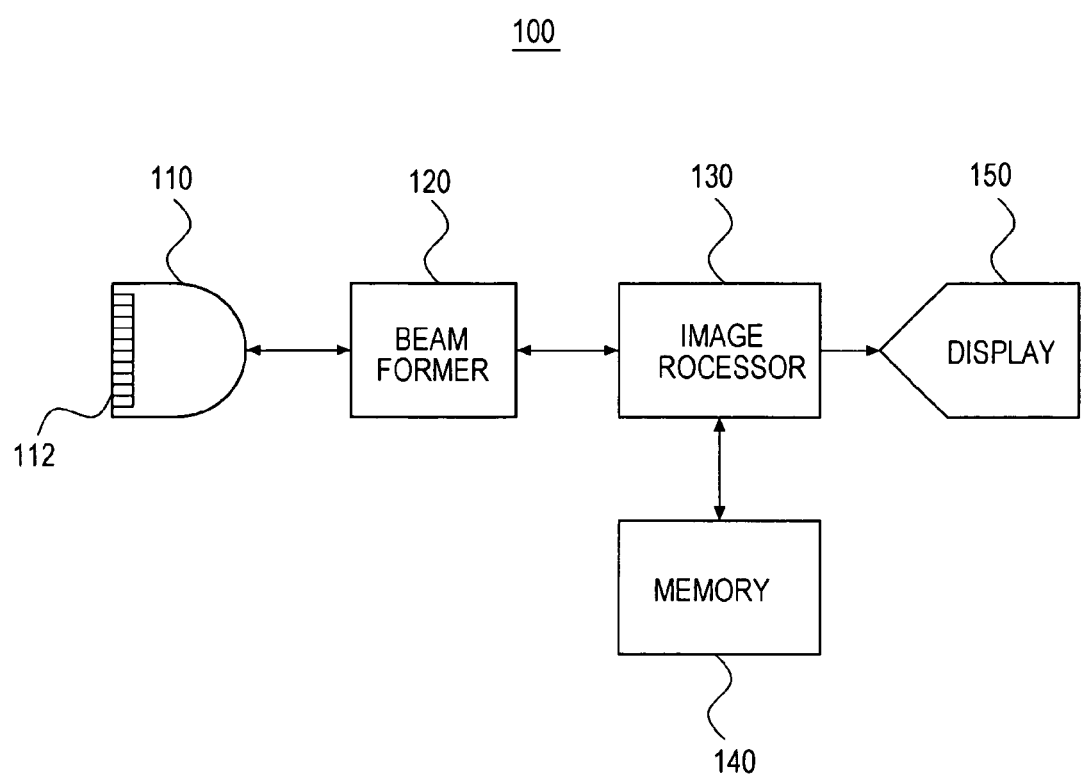
FIG. 1 is a block diagram showing an ultrasound diagnosis system in accordance with one embodiment of the present invention.

Hereinafter, the embodiments of the present invention will be described by referring to FIGS. 1 to 13. FIG. 1 is a block diagram showing an ultrasound diagnostic image system, which is constructed in accordance with one embodiment of the present invention. As shown in FIG. 1, the ultrasound diagnostic image system 100 includes a probe 110, a beam former 120, an image processor 130, a memory 140 and a display unit 150. The probe 110 has a one-dimensional (1D) or 2D array transducer 112 to transmit an ultrasound wave to the target object and receive the ultrasound wave signal (echo signal) reflected from the target object. The beam former 120 controls transmission and reception by the probe 110, and processes the received echo signal to form a coherent beam of the echo signal from the target object. The image processor 130 analyzes the echo signal delivered from the beam former 120 to perform image processing in accordance with one embodiment of the present invention. More specific description on the image processor 130 is given by reference to FIGS. 2 to 13. The ultrasound diagnostic image processed by the image processor 130 is stored in a memory 140 or displayed on the display unit 150.

Hereinafter, a method of automatically detecting a left ventricle boundary of the heart will be explained to facilitate the understanding of the present invention. FIG. 2A shows an exemplary filter for detecting a vertical edge of the ultrasound diagnostic image of the heart in accordance with one embodiment of the present invention. FIG. 2B shows an exemplary filter for detecting a horizontal edge of the ultrasound diagnostic image of the heart in accordance with one embodiment of the present invention.

The image processor 130 detects a heart edge from the heart ultrasound diagnostic image acquired by the ultrasound diagnostic system by using the filters shown in FIGS. 2A and 2B, thereby producing the edge detection boundary model. As to the process of producing the edge detection boundary model, more detailed descriptions will be given in view of FIGS. 2A, 2B, 3, 4A, 4B and 5A to 5D.

Figure 3:
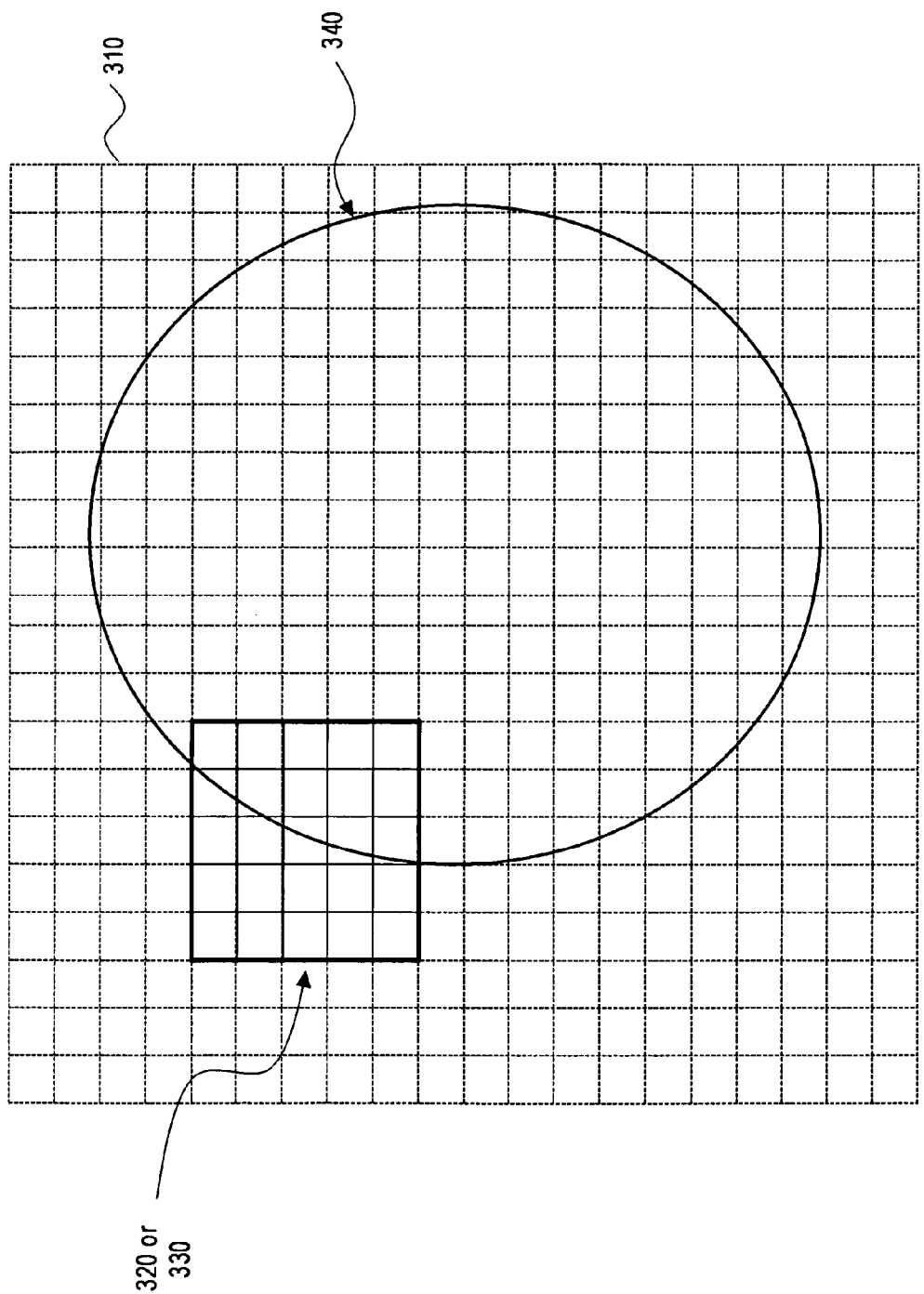
FIG. 3 is an exemplary diagram showing an edge detection filter and the ultrasound diagnostic image of the heart displayed with gray levels in accordance with one embodiment of the present invention.

FIG. 3 is an exemplary diagram showing an edge detection filter and the ultrasound diagnostic image of the heart displayed with gray levels in accordance with one embodiment of the present invention. The image processor 130 transforms an ultrasound diagnostic image of the heart first acquired by using the ultrasound diagnostic system to an ultrasound diagnostic image 310 with a gray level. The image processor 130 applies a vertical or a horizontal edge detection filter 320 or 330, as represented by Equation 1, to each gray level of the ultrasound diagnostic image 310, thereby detecting the characteristic value of each pixel.

$$g(x, y) = \left| \sum_s \sum_t w(x, t) f(x+s, y+t) \right| \quad \text{Equation 1}$$

wherein f(x,y) represents a gray level of each pixel of the ultrasound diagnostic image first acquired by the ultrasound diagnostic system, w(x,t) presents a vertical or horizontal edge detection filter, g(x,y) shows a characteristic value of the pixel to which the vertical or the horizontal edge detection filter is applied, and s and t indicate a filter size such that s and t have a value between −2 and 2 for a 5×5 size filter as shown in FIGS. 2A and 2B.

Further, the image processor 130 detects a heart edge by using the detected characteristic value to produce the edge detection boundary candidate model. More specific descriptions will be given below as to the procedure of detecting the characteristic value of each pixel by using the vertical edge detection filter 320 and the procedure of detecting the vertical edge of the heart by using the detected characteristic value.

Step (A1)

The edge detection filter 320 is applied to the gray level of each pixel of the ultrasound diagnostic image 310 in a row direction to detect a vertical characteristic value of each pixel. For example, as shown in FIG. 4A, the image processor 130 selects a reference pixel and pixels around the reference pixel by matching a center of the vertical edge filter (C2,R2) shown in FIG. 2A with the pixel (x2,y2) of the ultrasound diagnostic image 410 to calculate the vertical characteristic value g(2,2) of the gray level f(2,2) of the reference pixel represented by a coordinate (x2, y2) of the ultrasound diagnostic image 410. In this case, the selected number of pixels is identical to the size of the filter. In case a 5×5 size filter is used as shown in FIG. 2A, the selected number of pixels becomes 25.

A first additive value is obtained by adding each value of f(x0~x1, y0~y4), i.e., the gray levels of the ultrasound diagnostic image corresponding to 10 pixels of 2 columns, C0 and C1, which are at the left side of a center column C2 of the vertical edge detection filter among the selected 25 pixels. A second additive value is obtained by adding each value of f(x3~x4, y0~y4), i.e., the gray levels of the ultrasound diagnostic image corresponding to 10 pixels of 2 columns, C3 and C4, which are at the right side of the center column C2.

The image processor 130 obtains a difference between the first additive value (i.e., 0+1+2+4+0+3+3+1+1+2=17) and the second additive value (i.e., 4+9+3+4+8+7+2+8+9+6=60). The image processor 130 calculates the vertical characteristic value g(x2,y2) of the corresponding pixel (x2,y2) by taking an absolute value of the obtained difference. That is, the image processor 130 calculates 43 as the vertical characteristic value of the gray level f(x2, y2) of the corresponding pixel (x2, y2).

The above-described process is applied to the rest of the pixels in the same way. Finally, the image processor 130 calculates the vertical characteristic value of each pixel.

Step (A2)

The vertical characteristic values calculated by the Step (A1) are analyzed on a unit of row, and the pixels are arranged in order of magnitudes of the vertical characteristic values for each row.

Step (A3)

Among the arranged characteristic values by the step (A2), a predetermined number, preferably 20, of the vertical characteristic values are selected according to the magnitude for each row. In this step, however, the selected vertical characteristic values mostly correspond to the pixels representing the partition wall of the left ventricle and middle walls of the left and right ventricles. Thus, only the edge of the partition wall of left ventricle and middle walls of the left and right ventricles may be detected.

Step (A4)

Among the pixels corresponding to the vertical characteristic values selected at the Step (A3), the right most pixel having the largest x-axis coordinate value is determined. Then, starting from the vertical characteristic value corresponding to a pixel whose x-axis coordinate is next to that of the determined right most pixel, 10 more vertical characteristic values are selected in order of magnitude. By performing this step, it is possible to calculate the vertical characteristic values corresponding to a partition wall of the right ventricle and accordingly to detect the edge corresponding to the partition wall of the right ventricle.

Step (A5)

Figure 5A:
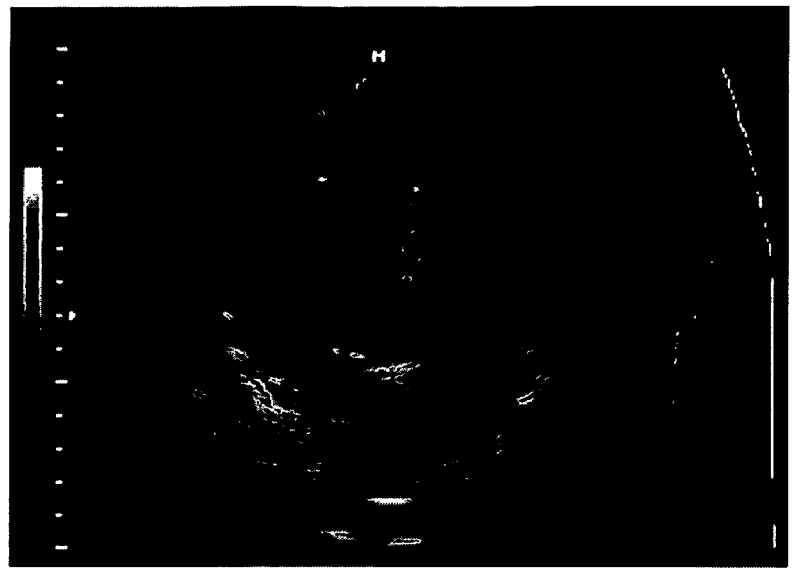
FIG. 5A shows an ultrasound diagnostic image before passing through the filters of FIGS. 2A and 2B.
Figure 5B:
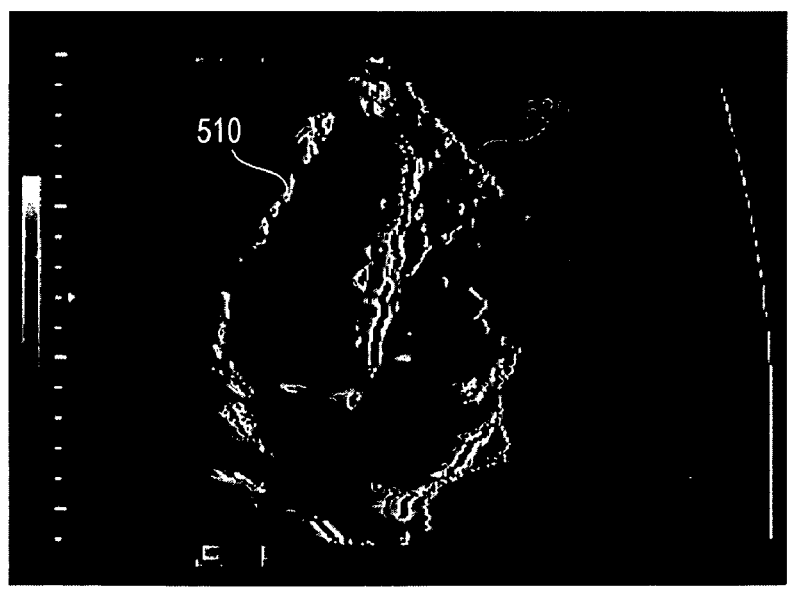
FIG. 5B shows an ultrasound diagnostic image after passing the image of FIG. 5A through the vertical edge detection filter of FIG. 2A.

By the Steps (A3) and (A4), the image processor 130 determines, as a vertical edge of the heart, a position of the pixels corresponding to the vertical characteristic values from the ultrasound diagnostic image shown in FIG. 5A, and detects the vertical edge of the heart as shown in FIG. 5B. In FIG. 5B, the reference numeral 510 represents a result of the process (A3), the reference numeral 530 represents a result of the process (A4), and the reference numeral 520 shows a position of the pixel having the largest vertical characteristic value in the process (A3).

Hereinafter, descriptions will be provided as to the process of calculating a horizontal characteristic value calculated by using the horizontal edge detection filter 330 and detecting the horizontal edge (more specifically positions of a valve and an apex) by using the calculated horizontal characteristic value.

Step (B1)

The horizontal edge detection filter is applied to the gray level of each pixel of the ultrasound diagnostic image 310 in the column direction to calculate a horizontal characteristic value of each pixel. For example, as shown in FIG. 4B, the image processor 130 selects a reference pixel and pixels around the reference pixel as many as a filter size to calculate the horizontal characteristic value g(2,2) of the gray level f(2,2) of the reference pixel represented by the coordinate x2 and y2 of the ultrasound diagnostic image 410. In this case, the selection of pixels may preferably be done by matching a center of the horizontal edge filter, i.e., (C2,R2) as shown in FIG. 2A with the pixel (x2, y2) of the ultrasound diagnostic image 410. Next, a third additive value is obtained by adding f(x0~x4, y0~y1), i.e., the gray levels of the ultrasound diagnostic image corresponding to 10 pixels of 2 rows, i.e., R0 and R1, which are at the upper side of a center row R2 of the horizontal edge detection filter among the selected pixels.

A fourth additive value is obtained by adding f(x0~x4, y3~y4), i.e., the gray levels of the ultrasound diagnostic image corresponding to 10 pixels of 2 rows, R3 and R4, which are at the lower side of the center row R2 of the horizontal edge detection filter. The image processor 130 obtains a difference between the third additive value (i.e., 0+1+3+4+9+2+4+9+3+4=39) and the fourth additive value (i.e., 3+1+7+2+8+1+2+2+9+6=41), and calculates the horizontal characteristic value by taking an absolute value of the obtained difference. That is, the image processor 130 selects 2 as a horizontal characteristic value (g(2,2)) of the pixel (f(2,2)) corresponding to the coordinate of x2 and y2.

The above-described Step (B1) is applied to the rest of the pixels in the same way. Finally, the image processor 130 calculates the horizontal characteristic value of each pixel.

Step (B2)

The horizontal characteristic values calculated by the Step (B1) are analyzed on a unit of column, and the pixels are ordered according to the magnitude of the horizontal characteristic value for each column.

Step (B3)

Among the ordered characteristic values by the process of (B2), a predetermined number, preferably 10, of horizontal characteristic values are selected in order of the magnitude for each column. Also, a position of the pixels corresponding to the selected horizontal characteristic values is determined as a horizontal edge of the heart.

Figure 5C:
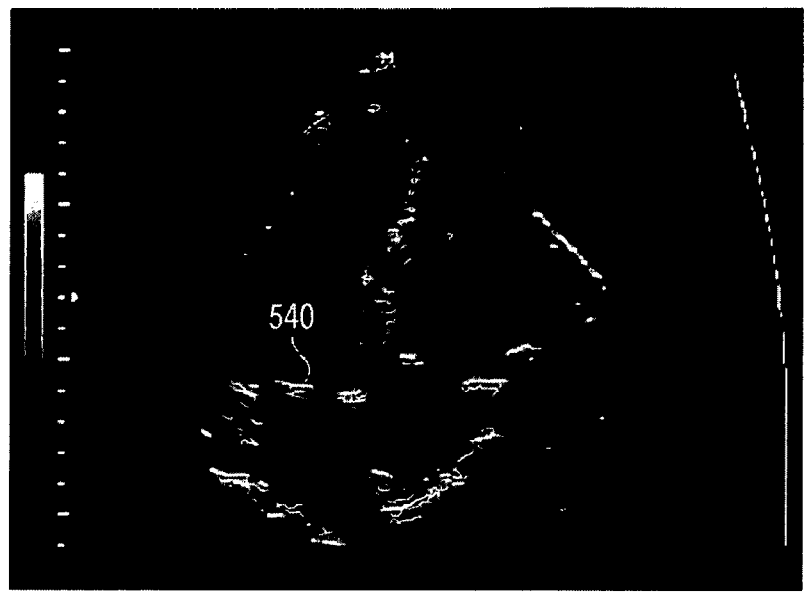
FIG. 5C shows an ultrasound diagnostic image after passing the image of FIG. 5A through the horizontal edge detection filter of FIG. 2B.

By the above-mentioned step, the image processor 130 detects the horizontal edge of the heart as shown in FIG. 5C. In FIG. 5C, the reference numeral 540 represents a result of the Step (B3).

Figure 5D:
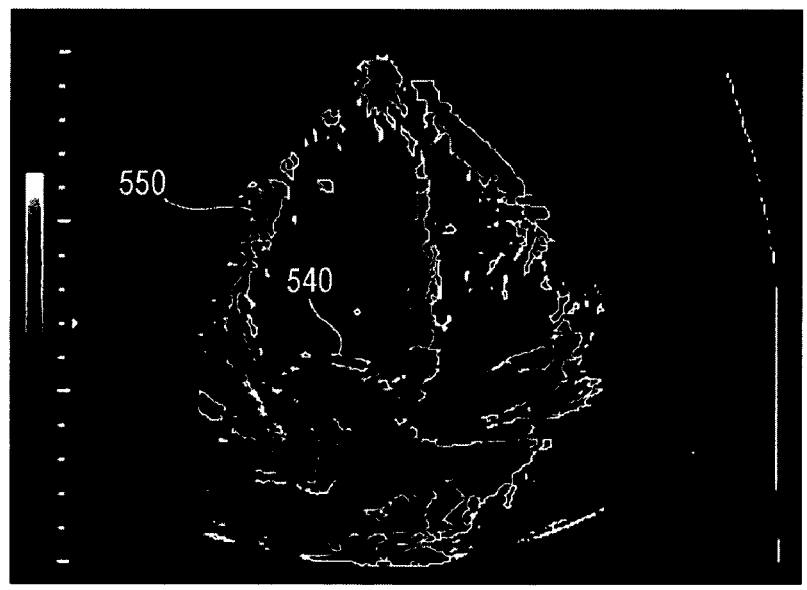
FIG. 5D shows an ultrasound diagnostic image obtained after passing the image of FIG. 5A though the filters of FIGS. 2A and 2B.

Next, the image processor 130 produces the edge detection boundary candidate model of the heart as shown in FIG. 5D by using the vertical and the horizontal edges detected according to the aforementioned steps. In FIG. 5D, the reference numeral 550 represents the vertical edge region detected by using the vertical edge detection filter 320, and the reference numeral 540 represents the horizontal edge region detected by using the horizontal edge detection filter 330.

Subsequently, the image processor 130 performs a simplification process to the edge detection boundary candidate model (refer to FIG. 5D) produced by the above-mentioned steps, thereby producing a simplification boundary candidate model. The simplification process consists of a morphological operation for performing a morphological conversion process, and a connected component labeling operation for attaching a single unique label to each pixel in the same connected component by searching all connected components of the ultrasound diagnostic image.

The morphological operation includes a modified erosion operation, a reduction operation and a dilation operation. The morphological operation will be described more specifically with reference to FIGS. 6A, 6B, 7A and 7B.

The erosion operation is performed to eliminate or reduce a small object in a whole image. Specifically, in case of using a 3×3 erosion mask for simplicity of calculation, a value of 1 is assigned to the pixel if an original image is correctly matched with an erosion mask and a value of 0 is assigned thereto if an original image is not precisely matched with an erosion mask. In accordance with one embodiment of the present invention, a 4×4 modified erosion mask may be preferably used to connect a disconnected portion and remove a small noise in the edge detection boundary candidate model (refer to FIG. 5D). The process of performing the modified erosion operation to the edge detection boundary candidate model by using the 4×4 modified erosion mask will be described more specifically with reference to FIGS. 6A and 6B.

Figure 6A:
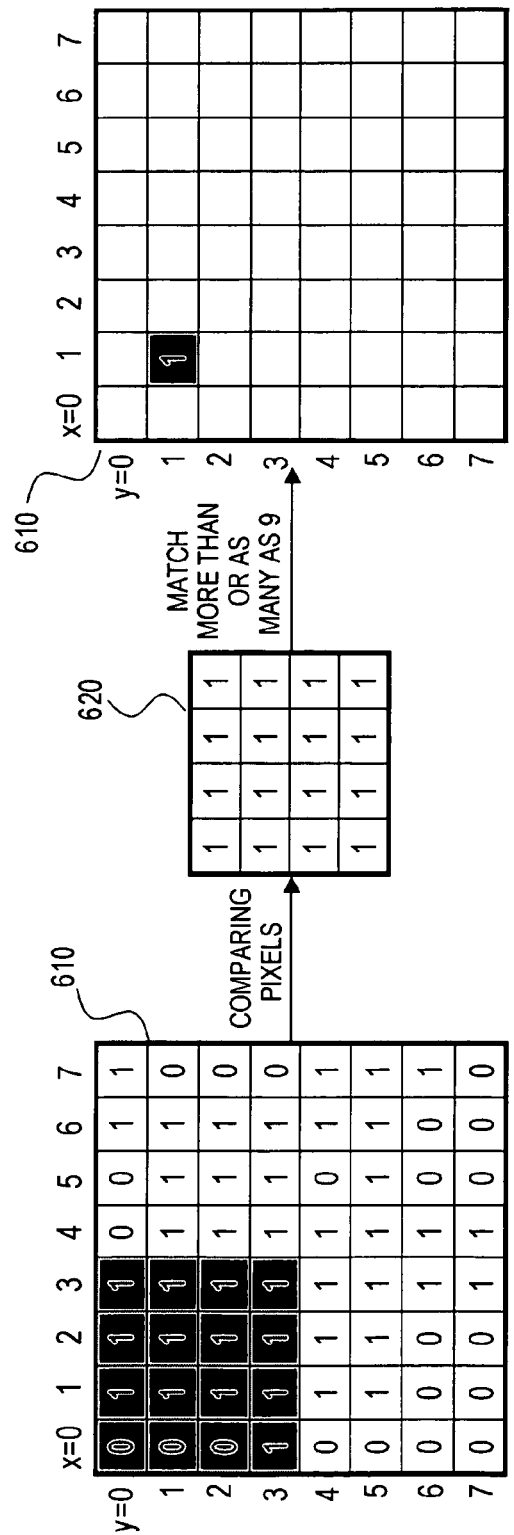
FIGS. 6A and 6B present a procedure of a modified needle invasive operation using a 4×4 modified needle invasive mask in accordance with one embodiment of the present invention.
Figure 6B:
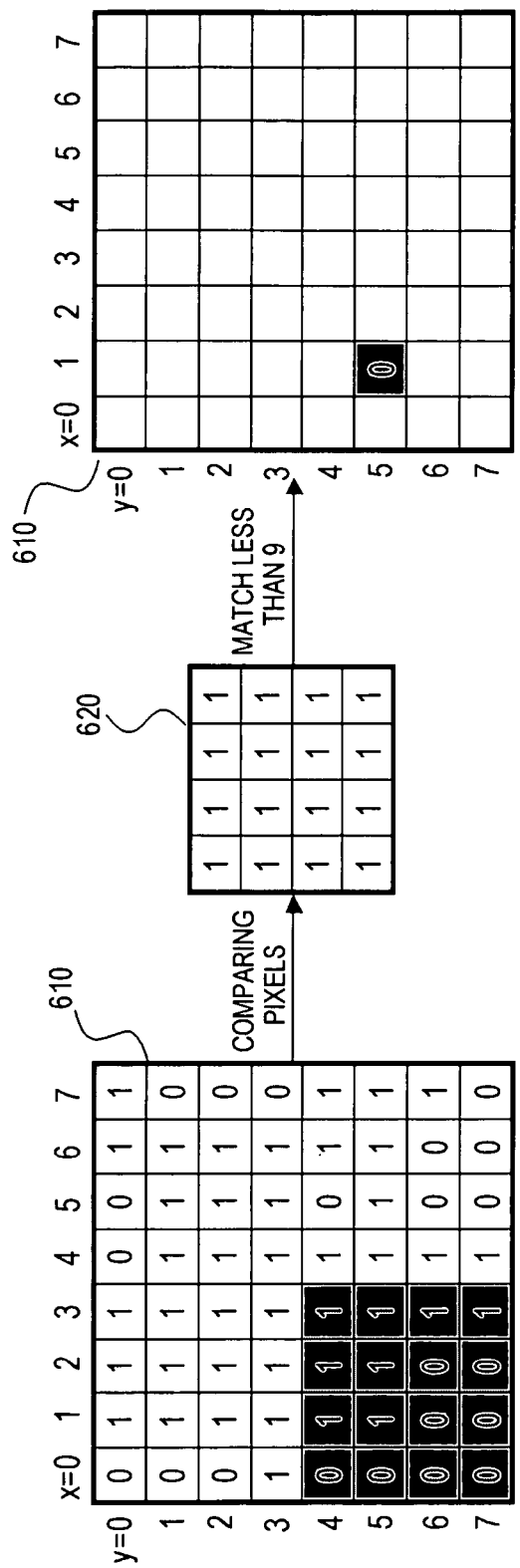

As shown in FIGS. 6A and 6B, the image processor 130 compares the 4×4 modified erosion mask with a corresponding pixel of the edge detection boundary candidate model 610 and pixels around the corresponding pixel, thereby assigning 1 to the corresponding pixel if matches occur more than or as many as a predetermined number and assigns 0 thereto if matches occur less than the predetermined number. More specifically, in order to perform the modified erosion operation upon the pixels corresponding to the coordinate of x1 to y1 in the edge detection candidate model 610 as shown in FIG. 6A, the image processor 130 compares the 4×4 modified erosion mask 620 with the pixels corresponding to columns of x0 to x3 and rows of y0 to y3 in the edge detection candidate model 610. Upon determining that 13 of pixels are matched, 1 is assigned to the coordinate of x1 to y1 of the edge detection candidate model 610.

Meanwhile, the image processor 130 compares the 4×4 modified erosion mask 620 with the pixels corresponding to columns of x0 to x3 and rows of y4 to y7 in the edge detection candidate model 610. Upon determining that 8 of pixels are matched, 0 is assigned to the coordinates of x1 and y5 of the edge detection candidate model 610. In this fashion, the image processor 130 performs the modified erosion operation upon the pixels corresponding to the coordinates of x1 to y5 in the edge detection candidate model 610 as shown in FIG. 6B.

Figure 7A:
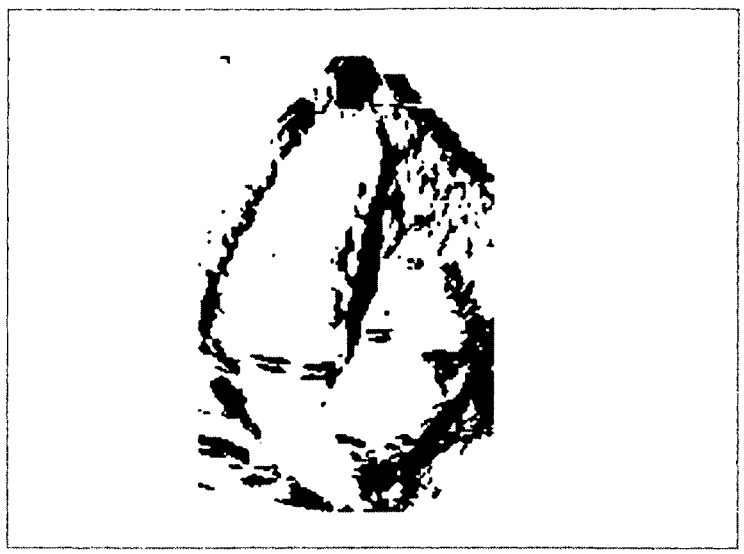
FIG. 7A shows an ultrasound diagnostic image before performing the modified needle invasive operation in accordance with one embodiment of the present invention.
Figure 7B:
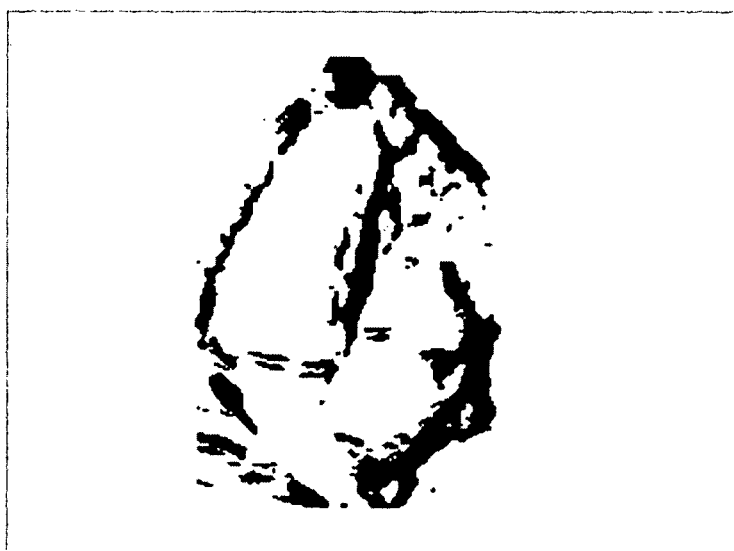
FIG. 7B shows an ultrasound diagnostic image after performing the modified needle invasive operation in accordance with one embodiment of the present invention.

By performing the aforementioned modified erosion operation, the small noise in the edge detection boundary candidate model shown in FIG. 7A can be removed without damaging the edge detection boundary candidate model as shown in FIG. 7B.

After the modified erosion operation is performed upon the edge detection boundary candidate model, the reduction operation is performed to reduce the size of the edge detection boundary candidate model. Preferably, the image processor 130 may use Equation 2 below to reduce the edge detection boundary candidate model.

$$(x',y')=(x/T_x, y/T_y)$$ Equation 2 wherein x and y represent coordinate of the edge detection boundary candidate model upon which the modified erosion operation has been performed, x' and y' are coordinate of the edge detection boundary candidate model upon which the reduction operation has been performed, and $T_x$ and $T_y$ are reduction factors.

By performing the reduction operation, the image processor 130 can shorten the distance between the unconnected edges in the edge detection boundary candidate model, upon which the modified erosion operation was performed. However, although the reduction operation can only shorten the distance between the unconnected edges, the disconnected region having short distance may not be completely connected.

Thus, after the reduction operation was performed upon the edge detection boundary candidate model, the dilation operation is performed in order to dilate an outermost pixel of the edge detection boundary candidate model, and fill an empty space such as a hole in the edge detection boundary candidate model, or connect the short disconnected region. The image processor 130 performs the above-mentioned operations to connect the unconnected edges in the edge detection boundary candidate model where the reduction operation was performed. Then, the image processor 130 performs the reduction operation again upon the edge detection boundary candidate model dilated by the dilation operation, thereby restoring to the original size by filling the hole in the edge detection boundary candidate model.

Figure 8A:
FIG. 8A shows an ultrasound diagnostic image after performing a morphological operation in accordance with one embodiment of the present invention.
Figure 8B:
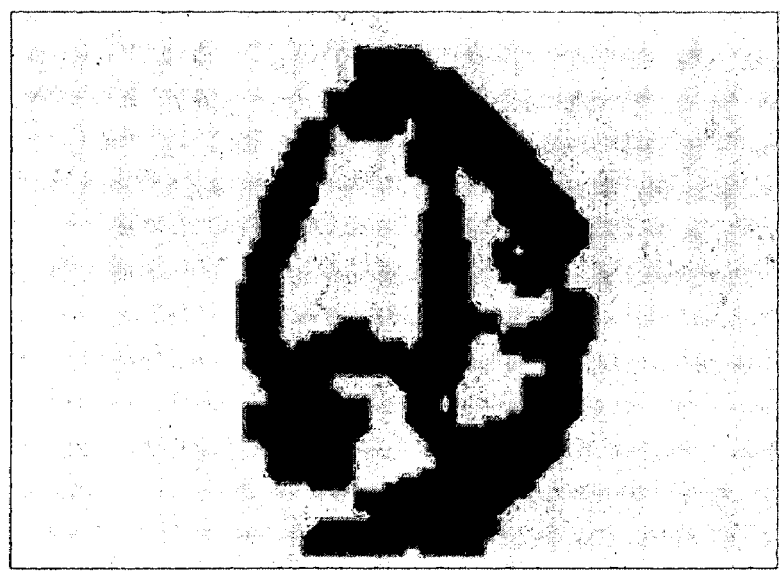
FIG. 8B shows an ultrasound diagnostic image after performing a connected component labeling operation in accordance with one embodiment of the present invention.

Subsequently, as shown in FIG. 8B, the image processor 130 performs a connected component labeling operation to remove the noise component in the edge detection boundary candidate model, upon which the morphological operation has been performed as shown in FIG. 8A. The connected component labeling operation discriminates the heart from the noise. To remove the distinguished noise, a sequential connected component algorithm with 4-connectivity may preferably be used so that a simplification boundary candidate model is produced.

Next, the image processor 130 applies a sessionization algorithm to the simplification boundary candidate model and produces a sessionization boundary candidate model. Herein, the sessionization algorithm is employed to convert an image represented by a thick region to an output image represented by a narrow line with a thickness of one pixel (more specifically a center line).

A process of determining a seed point and a maximum radiation radius will now be described in more detail in conjunction with FIGS. 9A to 9C and FIG. 10. The seed point and the maximum radiation radius are required to automatically detect a boundary line of the left ventricle of the heart based on the above-mentioned edge detection boundary candidate model, the simplification boundary candidate model and the sessionization candidate model.

The image processor 130 detects the vertical and the horizontal characteristic values of each pixel of the ultrasound diagnostic image by using the vertical and horizontal edge detection filters shown in FIGS. 2A and 2B, respectively. The image processor 130 sets 4 characteristic lines (the partition wall of the left ventricle, the middle partition of the left ventricle, the middle partition of the right ventricle and the partition wall of the right ventricle), the apex line and a bicuspid valve line in the edge detection boundary candidate model.

Figure 9A:
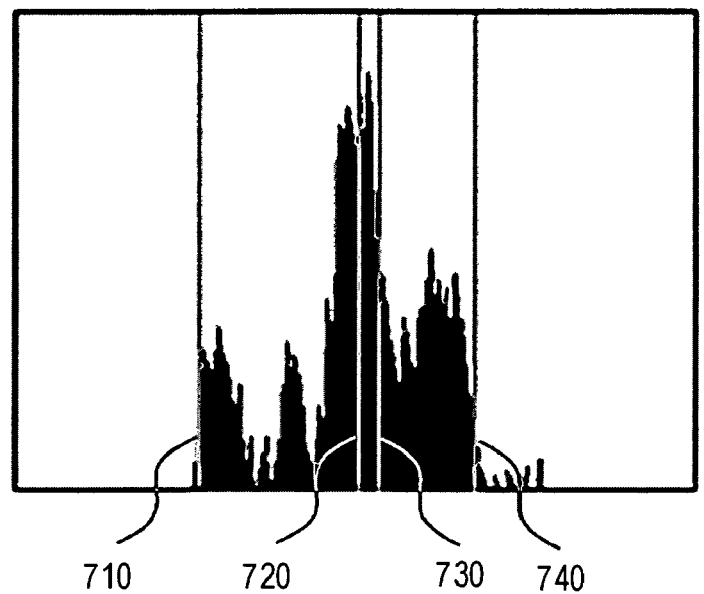
FIG. 9A presents an accumulative distribution chart created by using a pixel characteristic value and four characteristic lines detected by using the accumulative distribution chart in accordance with one embodiment of the present invention.
Figure 9B:
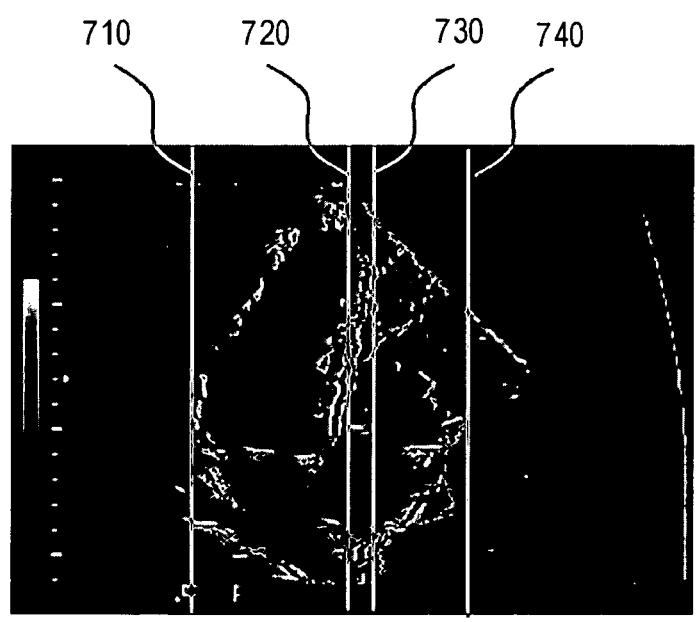
FIG. 9B shows an accumulative distribution chart after applying the four characteristic lines detected from FIG. 9B to an edge detection boundary model.
Figure 10:
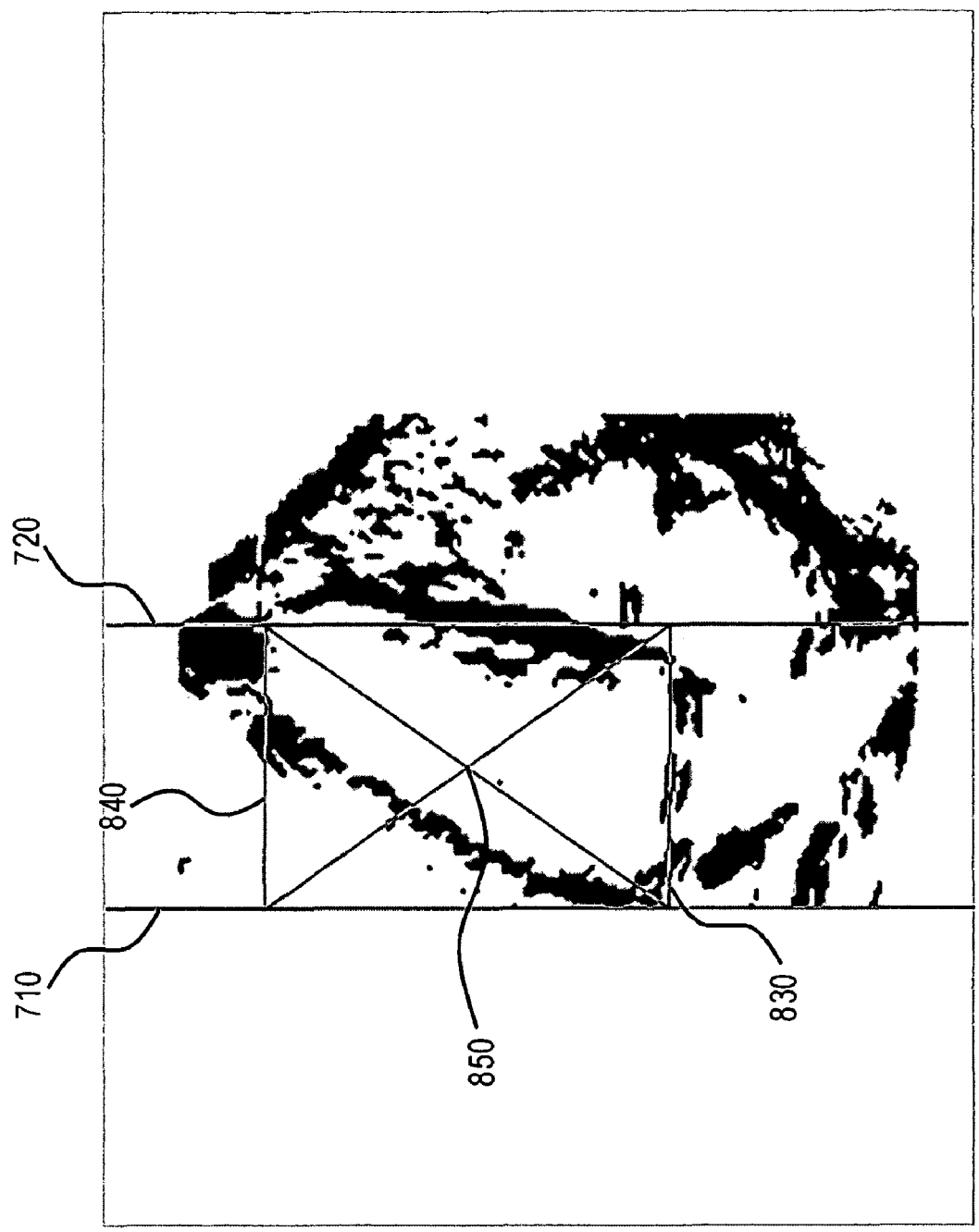
FIG. 10 depicts four characteristic lines and a seed point in accordance with one embodiment of the present invention.
Figure 11:
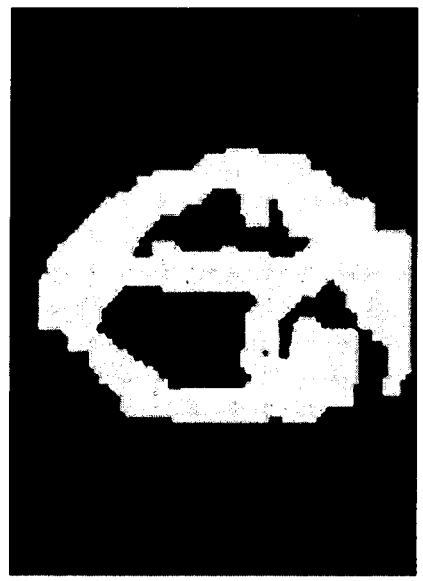
FIG. 11 shows an edge detection boundary model, a simplification boundary candidate model and a sessionization candidate model in accordance with one embodiment of the present invention.
Figure 11:
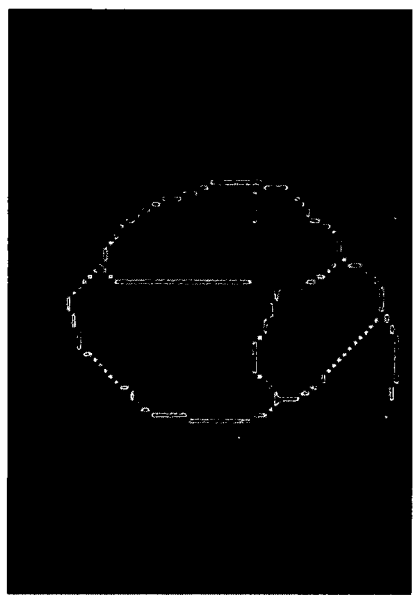
Figure 11:

Specifically, the image processor 130 makes a cumulative distribution chart as shown in FIG. 9A based on the vertical and the horizontal characteristic values of the ultrasound diagnostic image detected by the vertical edge detection filter shown in FIG. 2A. Next, the image processor 130 detects a starting portion of a left most peak by analyzing the cumulative distribution chart of FIG. 9A to set the starting portion of the left most peak as the partition wall 710 of the left ventricle and to set a starting portion of the highest peak as the middle partition line 720 of the left ventricle. Further, the image processor 130 sets an ending portion of the highest peak as the middle partition line 730 of the right ventricle and sets an ending portion of a right most peak as the partition wall line 740 of the right ventricle. In this case, the image processor 130 may remove the noise in the outside portion of the heart of the ultrasound diagnostic image by using the partition wall line of the left ventricle 710 and that of the right ventricle 740.

Meanwhile, the image processor 130 makes a cumulative distribution chart (not shown) in the same way as described above based on the characteristic values of the ultrasound diagnostic image detected by the horizontal edge detection filter shown in FIG. 2B. Next, the image processor 130 analyzes the above-made cumulative distribution chart to set the starting portion of the left most peak to the apex line 840 and set a starting portion of a right most peak to the bicuspid valve line 830.

Next, the image processor 130 sets a center of a diagonal line of a rectangular as a seed point 850, the rectangular being composed of the partition wall line of the left ventricle 710, the middle partition line of the left ventricle 720, the bicuspid valve line 830 and the apex line 840. Further, the image processor 130 sets a distance between the seed point 850 and vertexes of the rectangular to a maximum radiation radius R. That is, ½ of the diagonal line length is set to the maximum radiation radius R. The radiation radius R is set to its maximum value to prevent the left ventricle boundary from being searched outside of the left ventricle boundary when the image processor 130 operates to radiate the left ventricle boundary at the seed point 850.

Once the seed point 850 and the maximum radiation radius R are set by the aforementioned processes, the image processor 130 automatically detects the boundary line of the left ventricle of the heart from the edge detection boundary candidate model (FIG. 11A), the simplification boundary candidate model (FIG. 11B) and the sessionization boundary candidate model (FIG. 11C) by using the seed point 850 and the maximum radiation radius R. The description on the processes of automatically detecting the boundary line of the left ventricle is given below with reference to FIGS. 11 to 13.

(1) The image processor 130 operates to radiate to the maximum radiation radius R in a radial direction at the seed point 850 in the edge detection boundary candidate model (FIG. 11A) and the simplification boundary candidate model (FIG. 11B), thereby recognizing the existence of the left ventricle boundary.

(2) If both the edge detection boundary candidate model (FIG. 11A) and the simplification boundary candidate model (FIG. 11B) are recognized to have the left ventricle boundary, the image processor 130 detects a position of the left ventricle boundary of the edge detection boundary candidate model.

(3) The image processor 130 sets the left ventricle boundary point to the position corresponding to the ultrasound diagnostic image (FIG. 5A) first acquired by the ultrasound diagnostic system based on the detected position of the left ventricle in the process (2) above.

(4) The image processor 130 repeats the processes (1) to (3) by a predetermined interval with reference to the seed point 850.

(5) If one of the edge detection boundary candidate model (FIG. 11A) and the simplification boundary candidate model (FIG. 11B) is recognized not to include the left ventricle boundary, the image processor 130 detects an average position between the left ventricle boundary position of the simplification boundary candidate model (FIG. 11B) and that of the sessionization boundary candidate model (FIG. 11C).

(6) The image processor 130 sets the left ventricle boundary point to the position corresponding to the ultrasound diagnostic image (FIG. 5A) first acquired by the ultrasound diagnostic system based on the average position detected in the process (5) above.

Figure 12:
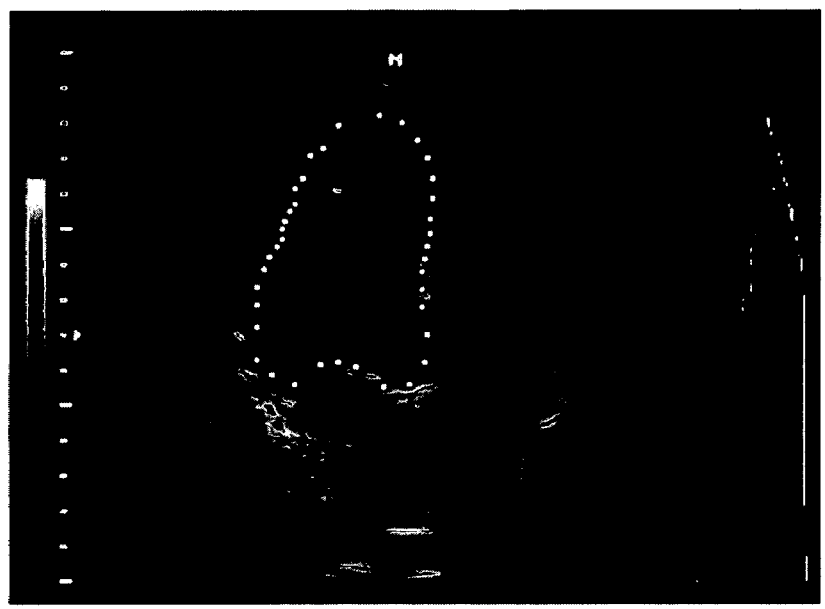
FIG. 12 shows a detected boundary point in accordance with one embodiment of the present invention.

By the aforementioned processes, the image processor 130 sets a predetermined number, preferably 40, of left ventricle boundary points as shown in FIG. 12. The above processes can be represented numerically as following Equation 3:

Contour={SE∩EA} if (Contour==φ)

Contour={average(SE,TE)}    Equation 3 wherein EA is an edge detection boundary candidate model of FIG. 11A, SE is a simplification boundary candidate model of FIG. 11B, TE is a sessionization boundary candidate model of FIG. 11C, and Contour={SE∩EA} represents that both SE and EA have the left ventricle boundary, if (Contour==φ) means that one of SE and EA has a disconnected boundary, and Contour={average (SE, TE)} represents that an average of SE and TE is decided as a boundary point for a null set of SE and EA.

Figure 13:
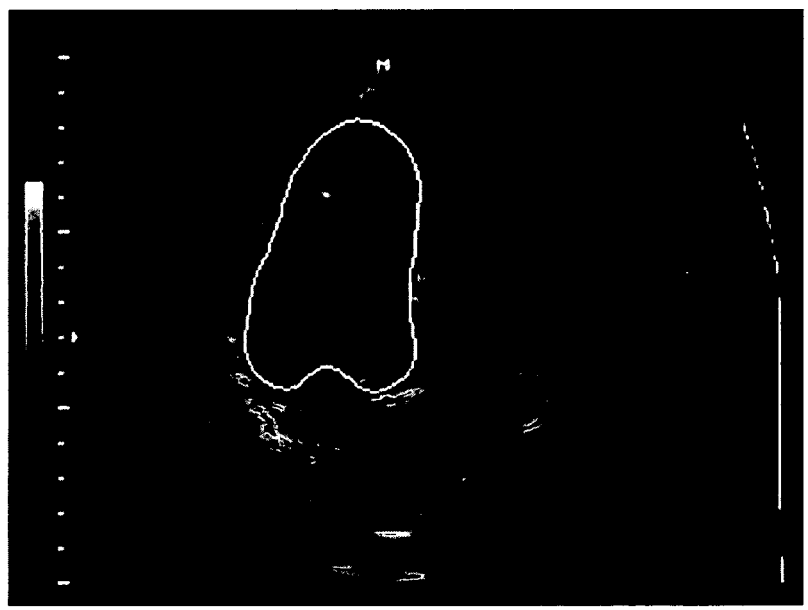
FIG. 13 shows an image in which Bezier spline is applied to the boundary point of FIG. 12.

Next, as shown in FIG. 13, the image processor 130 applies the Beizier Spline to the detected left ventricle boundary point, thereby modeling the left ventricle boundary line. More specifically, the image processor 130 models the candidate of the boundary per each left ventricle boundary point detected, detects the boundary line point from the candidate model of the boundary line, then obtains the beizier line by using the detected boundary line point, and connects an inner membrane of the heart with a soft curve.

In accordance with the aforementioned present invention, the boundary of the target object is automatically detected by using the ultrasound diagnostic image. This is so that the problem of the conventional method of detecting the boundary manually, i.e., that the measured result may vary with each operator, can be prevented.

While the present invention has been shown and described with respect to a preferred embodiment, those skilled in the art will recognize that various changes and modifications may be made without departing from the spirit and scope of the invention as defined in the appended claims.

What is claimed is:

1. A method of detecting a boundary of a target object from an ultrasound diagnostic image having a plurality of pixels using an image processor in an ultrasound diagnostic system, the method comprising:
   (a) filtering, via the image processor, the ultrasound diagnostic image to
      calculate a vertical characteristic value and a horizontal characteristic value of each of the plurality of pixels,
      detect at least one vertical edge of the target object from the ultrasound diagnostic image based on the vertical characteristic value,
      detect at least one horizontal edge of the target object from the ultrasound diagnostic image based on the horizontal characteristic value, and
      form an edge detection boundary candidate model based on the at least one vertical edge and the at least one horizontal edge;
   (b) performing, via the image processor, a simplification operation upon the edge detection boundary candidate model to form a simplification boundary candidate model;
   (c) performing, via the image processor, a sessionization operation upon the simplification boundary candidate model to form a sessionization boundary candidate model; and
   (d) detecting, via the image processor, a boundary of the target object of the ultrasound diagnostic image based on the edge detection boundary candidate model, the simplification boundary candidate model and the sessionization boundary candidate model, wherein
   step (b) includes,
   (b1) performing a morphological operation to morphologically transform the edge detection boundary candidate model, and
   step (b1) includes, (b11) performing an erosion operation upon the edge detection boundary candidate model to connect an unconnected portion of the edge and remove a small noise, (b12) performing a reduction operation upon the edge detection boundary candidate model to connect the unconnected portion of the edge by reducing the size of the edge detection boundary candidate model, (b13) performing a dilation operation upon the edge detection boundary candidate model to expand outermost pixels, and (b14) performing the erosion operation upon the edge detection boundary candidate model to which the dilation operation was performed.

2. The method of claim 1, wherein the step (a) includes:

(a1) performing the filtering upon the ultrasound diagnostic image via a vertical edge detection filter to calculate the vertical characteristic values for detection of the at least one vertical edge of the target object from the ultrasound diagnostic image; and (a2) performing the filtering upon the ultrasound diagnostic image via a horizontal edge detection filter to calculate the horizontal characteristic values for detection of the at least one horizontal edge of the target object from the ultrasound diagnostic image.

3. The method of claim 2, wherein the step (a1) includes:

(a11) applying the vertical edge detection filter to each pixel of the ultrasound diagnostic image in a row direction to calculate the characteristic value of each pixel of the ultrasound diagnostic image;

(a12) analyzing the calculated characteristic values for each row to rank the characteristic values in order of magnitude;

(a13) determining a predetermined number of the ranked characteristic values in order of magnitude; and (a14) deciding positions of pixels corresponding to the determined characteristic values as positions of the edge.

4. The method of claim 3, wherein the step (a13) includes:

determining a rightmost pixel among the pixels corresponding to the determined characteristic values at each row, and determining a predetermined number of characteristic values again in order of magnitude starting from the characteristic value corresponding to a pixel positioned next to the rightmost pixel in a row direction.

5. The method of claim 2, wherein the step (a2) includes:

(a21) applying the horizontal edge detection filter to each pixel of the ultrasound diagnostic image in a column direction to calculate the characteristic value of each pixel of the ultrasound diagnostic image;

(a22) analyzing the calculated characteristic values for each column to rank the characteristic values in order of magnitude;

(a23) determining a predetermined number of the ranked characteristic values in order of magnitude of each characteristic value; and (a24) deciding positions of pixels corresponding to the determined characteristic values as positions of the edge.

6. The method of claim 1, wherein the edge is detected in the step (a) by the following equation:

$$g(x, y) = \left| \sum_{s=-2}^{2} \sum_{t=-2}^{2} w(x, t) f(x+s, y+t) \right|$$

wherein f(x,y) represents each pixel of the ultrasound diagnostic image, w(x,t) represents a vertical or the horizontal edge detection filter, g(x,y) shows a pixel to which the vertical or the horizontal edge detection filter is applied, and s and t indicate a filter size.

7. The method of claim 1, wherein the step (b) includes:

(b2) performing a connected component labeling operation upon the edge detection boundary candidate model to search connected components and attach a single unique label to the pixels in the same connected component.

8. The method of claim 1, wherein the step of (b11) includes:

(e1) comparing each pixel of the edge detection boundary candidate model and pixels adjacent to said each pixel with a mask with a predetermined size;

(e2) assigning one (1) to said each pixel, if said each pixel and pixels adjacent to said each pixel are determined to coincide with the mask by more than or as many as a predetermined number; and (e3) assigning zero (0) to said each pixel, if said each pixel and pixels adjacent to said each pixel are determined to coincide with the mask by less than the predetermined number.

9. The method of claim 1, wherein the reduction operation is performed in the step (b12) by the following equation:

$$(x',y')=x/T_x, y/T_y$$

wherein x and y represent coordinates of the edge detection boundary candidate model upon which the erosion operation was performed, Tx and Ty, are reduction factors, and x' and y' are coordinates of the edge detection boundary candidate model upon which the reduction operation was performed.

10. The method of claim 1, wherein the step (d) includes:

(d1) setting a predetermined number of characteristic lines to the edge detection boundary candidate model, the characteristic lines indicating an edge boundary;

(d2) detecting a seed point based on the characteristic lines;

(d3) setting a predetermined number of boundary points in the ultrasound diagnostic image based on the detected seed point, the edge detection boundary candidate model, the simplification boundary candidate model and the sessionaization boundary candidate model; and (d4) modeling a boundary line of the target object of the ultrasound diagnostic image by using the predetermined number of boundary points.

11. The method of claim 10, wherein the step (d1) includes:

(d11) setting a characteristic line of a vertical edge based on characteristic values of the ultrasound diagnostic image detected by a vertical edge detection filter; and (d12) setting a characteristic line of a horizontal edge based on the characteristic values of the ultrasound diagnostic image detected by a horizontal edge detection filter.

12. The method of claim 11, wherein the step (d11) includes:

(f1) creating a vertical edge accumulative distribution chart by using the characteristic values of the ultrasound diagnostic image detected by the vertical edge detection filter;

(f2) detecting a peak start and a peak end points of the accumulative distribution chart by analyzing the created vertical edge accumulative distribution chart; and (f3) setting the peak start and the peak end points as the characteristic line of the vertical edge.

13. The method of claim 11, wherein the step (d12) includes:
(g1) creating a horizontal edge accumulative distribution chart by using the characteristic values of the ultrasound diagnostic image detected by the horizontal edge detection filter;
(g2) detecting a peak start and a peak end points of the accumulative distribution chart by analyzing the created horizontal edge accumulative distribution chart; and
(g3) setting the peak start and the peak end points as the characteristic line of the horizontal edge.

14. The method of claim 10, wherein the step (d2) includes:
(d21) setting a center of a figure formed by the characteristic lines as the seed point; and
(d22) setting a distance between the set seed point and a vertex of the figure formed by the characteristic lines to a maximum radiation radius.

15. The method of claim 10, wherein the step (d3) includes:
(d31) analyzing a boundary of the edge detection boundary candidate model and a boundary of the simplification boundary candidate model in a radial direction from the seed point;
(d32) determining if a region exists, in which the boundaries of the edge detection boundary candidate model and the simplification boundary candidate model exist simultaneously; and
(d33) if it is determined that the region exists in the step (d32), then setting a position corresponding to the region of the ultrasound diagnostic image as a boundary point.

16. The method of claim 15, wherein the step (d3) further includes:
(d34) if it is determined that the region does not exist in the step (d32), then detecting an average region of boundary regions of the simplification boundary candidate model and the sessionization boundary candidate model; and
(d35) setting a position corresponding to the average region of the ultrasound diagnostic image as a boundary point.

17. The method of claim 10, wherein the step (d4) includes:
(d41) modeling a candidate of the boundary line at each boundary point;
(d42) detecting a boundary line point from the candidate of the boundary line; and
(d43) connecting the detected boundary line point with a curve.

18. The method of claim 17, wherein the step (d43) includes applying Bezier spline to the boundary line point to connect the boundary line point.

19. An ultrasound diagnostic system, which transmits an ultrasound wave to a target object, and receives an ultrasound signal reflected from the target object and thereby providing an ultrasound diagnostic image having a plurality of pixels, the system comprising:
an image processor including,
a first means for
filtering the ultrasound diagnostic image to calculate a vertical characteristic value and a horizontal characteristic value of each of the plurality of pixels,
detecting at least one vertical edge of the target object from the ultrasound diagnostic image based on the vertical characteristic value,
detecting at least one horizontal edge of the target object from the ultrasound diagnostic image based on the horizontal characteristic value, and
producing an edge detection boundary candidate model based on the at least one vertical edge and the at least one horizontal edge,
a second means for performing a simplification operation upon the edge detection candidate model to produce a simplification boundary candidate model,
a third means for performing a sessionization operation upon the simplification boundary candidate model to produce the sessionization boundary candidate model, and
a fourth means for detecting a boundary of the target object of the ultrasound diagnostic image based on the edge detection boundary candidate model, the simplification boundary candidate model and the sessionization boundary candidate model, wherein
the performing the simplification operation by the second means includes,
performing a morphological operation to morphologically transform the edge detection boundary candidate model, and
performing the morphological operation includes,
performing an erosion operation upon the edge detection boundary candidate model to connect an unconnected portion of the edge and remove a small noise,
performing a reduction operation upon the edge detection boundary candidate model to connect the unconnected portion of the edge by reducing the size of the edge detection boundary candidate model,
performing a dilation operation upon the edge detection boundary candidate model to expand outermost pixels, and
performing the erosion operation upon the edge detection boundary candidate model to which the dilation operation was performed.

20. The method of claim 19, wherein the first means includes
a vertical edge detection filter to calculate the vertical characteristic values for the detecting of the at least one vertical edge of the target object from the ultrasound diagnostic image, and
a horizontal edge detection filter to calculate the horizontal characteristic values for the detecting of the at least one horizontal edge of the target object from the ultrasound diagnostic image.

* * * * *